United States Patent [19]
Bruns et al.

[11] 4,083,876
[45] Apr. 11, 1978

[54] PROCESS FOR THE PREPARATION OF THIOGLYCOLS

[75] Inventors: Ludwig Bruns; Günther Schnuchel; Joachim Weber, all of Dormagen, Germany

[73] Assignee: Erdolchemie GmbH, Cologne, Germany

[21] Appl. No.: 698,561

[22] Filed: Jun. 22, 1976

[30] Foreign Application Priority Data

Jul. 3, 1975 Germany .............................. 2529646

[51] Int. Cl.² .......................................... C07C 148/00
[52] U.S. Cl. ............................................. 260/609 R
[58] Field of Search .................................. 260/609 R

[56] References Cited

U.S. PATENT DOCUMENTS 3,574,768   4/1971   Tompkins ..................... 260/609 R

FOREIGN PATENT DOCUMENTS 10,551   1/1973   U.S.S.R. ........................ 260/609 R

OTHER PUBLICATIONS

Chem. Abst. vol. 49, p. 10355.

Primary Examiner—Joseph Paul Brust
Assistant Examiner—Molly C. Eakin
Attorney, Agent, or Firm—Burgess, Dinklage & Sprung

[57] ABSTRACT

Thioglycols are prepared by reacting alkylene carbonates with hydrogen sulfide at 50° – 250° C in an inert solvent in the presence of a carbonate or bicarbonate of alkali or alkaline earth metal as catalyst for the reaction.

12 Claims, No Drawings

PROCESS FOR THE PREPARATION OF THIOGLYCOLS

BACKGROUND

The invention relates to an improved process for the preparation of thioglycols.

Processes for the preparation of thioglycol (2-mercaptoethynol) are known. For example, when ethylene oxide and hydrogen sulphide are reacted 2-mercaptoethanol is formed in yields of only 60% (compare F.N. Woodward Chem. Soc. (London) 1948, 1892). The yields are even poorer when, according to German Patent Specification 486,079, ethylene chlorohydrin and sodium bisulphide solution are used as the starting materials. Furthermore, it is known from U.S. Pat. No. 2,402,665 to prepare 2-mercaptoethanol in a technically involved process by high pressure hydrogenation of bis-(2-hydroxyethyl) trisulphide over cobalt sulphide catalysts. The known processes have the disadvantage that they either lead to undesired by-products or the products are accessible only by complicated and technically involved processes.

THE INVENTION

An improved process for the preparation of thioglycols has now been found, which is characterised in that the alkylene carbonate corresponding to the thioglycol to be produced is reacted with hydrogen sulphide at elevated temperatures and in an inert solvent in the presence of a catalyst.

Examples which may be mentioned of alkylene carbonates which are used for the process according to the invention are ethylene glycol carbonate, propylene glycol carbonate butylene glycol carbonate, the carbonic acid ester of 1,2-butanediol or also cyclic carbonates of polyols, especially glycerol carbonate. Ethylene glycol carbonate and propylene glycol carbonate are particularly preferred. Preferably, the glycol contains 2 to 4 carbon atoms.

The alkylene glycol carbonates which are used according to the process of the invention are known and can be prepared, for example, by reacting the corresponding olefine oxides with carbon dioxide in the presence of a catalyst (compare U.S. Pat. No. 2,773,070).

Catalysts which can be used for the process according to the invention are metal salts which have a catalytic influence on the decomposition of the alkylene carbonates into the corresponding epoxides and carbon dioxide. Preferred catalysts which may be mentioned are the carbonates and bicarbonates of the alkali metals and the alkaline earth metals, for example the carbonates and bicarbonates of sodium, potassium, rubidium, caesium, calcium, strontium and barium. Of course, mixtures of the catalysts mentioned can also be used.

The amount of catalyst which is employed is in itself not critical; appropriately, the catalyst is used in amounts of about 2–5% by weight, based on the alkylene carbonate employed.

The reaction according to the process of the invention is carried out at elevated temperatures, the temperature being so selected, depending on the alkylene carbonate employed and the catalyst which is used, that splitting of the glycol carbonate into the corresponding epoxide and carbon dioxide takes place. Appropriately, temperatures in the range from 50° to 250° C, preferably in the range from 130° to 160° C, are used.

The pressure under which the process according to the invention is carried out is not in itself critical and results from the amount of hydrogen sulphide employed for the reaction. In principle, hydrogen sulphide is employed in excess and the molar ratio of alkylene carbonate to hydrogen sulphide is generally between 1:2 and 1:20, and is preferably 1:3 to 1:10.

The solvents used as the inert solvent for the process according to the invention are preferably those in which hydrogen sulphide is readily soluble under the reaction conditions. Examples of solvents which may be mentioned are saturated aliphatic hydrocarbons with 6 to 16 carbon atoms or aromatic hydrocarbons, especially benzene hydrocarbons, and ethers which are inert under the reaction conditions, such as, for example, diethyl ether and dioxane. It has proved to be particularly advantageous to use hexanes, heptanes, octanes, dodecanes or benzene, toluene or xylenes as the solvents. Of course, mixtures of the solvents mentioned can also be used.

The amount of solvent which is used can vary within wide limits. It has proved to be particularly appropriate to employ an approximately 20–25% strength solution of the alkylene carbonate, which is used, in a solvent.

Compared with the state of the art, the process according to the invention is an improved, simple process for the preparation of thioglycols in improved yields.

The thioglycols obtainable by the process according to the invention are important intermediate products for the preparation of plant protection formulations and rubber auxiliaries.

EXAMPLE 1

88 g of glycol carbonate, 300 ml of benzene and 5 g of potassium carbonate are filled into a stirred autoclave with a capacity of 2 l. After closing the autoclave, 345 g of hydrogen sulphide are introduced under pressure, during which time the stirrer in the autoclave must be in operation. The pressure vessel is then warmed to 145° C for 3–4 hours. A pressure of about 70–80 bars is set up during this time. After cooling and letting-down, the solution of thioglycol in benzene was worked up by distillation. A total of 65 g of thioglycol had formed, the conversion of glycol carbonate being 90%. This amount corresponds to a selectivity of 92.7%.

EXAMPLES 2–5

Using the same apparatus, the catalysts sodium carbonate, potassium bicarbonate, calcium carbonate and barium carbonate were tested under the same experimental conditions. Table 1 shows the results of the experiments.

|  | Catalyst | Conversion | Selectivity for thioglycol |
|---|---|---|---|
| Example 2 | $Na_2CO_3$ | 84% | 94% |
| Example 3 | $KHCO_3$ | 89% | 92% |
| Example 4 | $BaCO_3$ | 87% | 95.5% |
| Example 5 | $CaCO_3$ | 86% | 91.0% |

What is claimed is:

1. Process for the preparation of a thioglycol from an alkylene carbonate of the group ethylene glycol carbonate, propylene glycol carbonate, butylene glycol carbonates and glycerol carbonates, wherein the alkylene carbonate is reacted with hydrogen sulphide at an elevated temperature in an inert solvent in which said hydrogen sulphide is readily soluble under the reaction conditions in the presence of a catalyst for the reaction, to form said thioglycol, said catalyst being of the group carbonates and bicarbonates of alkali metals and alkaline earth metals.

2. Process according to claim 1, wherein the reaction is carried out at a temperature of 50° – 250° C.

3. Process according to claim 1, wherein the solvent is a solvent for hydrogen sulphide.

4. Process according to claim 3, wherein the solvent is an aliphatic or aromatic hydrocarbon.

5. Process according to claim 3, wherein the solvent is of the group, hexanes, heptanes, octanes, dodecanes, benzene, toluene and xylenes.

6. Process according to claim 1, wherein the reaction is carried out at a temperature of 50° – 250° C, and the solvent is a solvent for hydrogen sulphide.

7. Process according to claim 6, wherein the solvent is an aliphatic or aromatic hydrocarbon.

8. Process according to claim 7, wherein the solvent is of the group hexanes, heptanes, octanes, dodecanes, benzene, toluene and xylene.

9. Process according to claim 1, wherein the alkylene carbonate is ethylene glycol carbonate.

10. Process according to claim 1, wherein the alkylene carbonate is propylene glycol carbonate.

11. Process according to claim 6, wherein the alkylene carbonate is ethylene glycol carbonate.

12. Process according to claim 6, wherein the alkylene carbonate is propylene glycol carbonate.

* * * * *